United States Patent
Fleischman et al.

(10) Patent No.: US 6,749,568 B2
(45) Date of Patent: *Jun. 15, 2004

(54) INTRAOCULAR PRESSURE MEASUREMENT SYSTEM INCLUDING A SENSOR MOUNTED IN A CONTACT LENS

(75) Inventors: Aaron J. Fleischman, University Heights, OH (US); Shuvo Roy, Cleveland, OH (US); Hilel Lewis, Beachwood, OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 50 days.

This patent is subject to a terminal disclaimer.

(21) Appl. No.: 10/128,321

(22) Filed: Apr. 22, 2002

(65) Prior Publication Data

US 2002/0193674 A1 Dec. 19, 2002

Related U.S. Application Data

(63) Continuation-in-part of application No. 09/642,573, filed on Aug. 21, 2000, now Pat. No. 6,447,449.

(51) Int. Cl.⁷ .................................. A61B 3/16
(52) U.S. Cl. .................. 600/399; 600/405; 600/561
(58) Field of Search .................. 600/398, 399, 600/400, 405, 406, 561, 587

(56) References Cited

U.S. PATENT DOCUMENTS

| | | |
|---|---|---|
| 4,089,329 A | 5/1978 | Couvillon, Jr. et al. |
| 4,305,399 A | 12/1981 | Beale |
| 4,628,938 A | 12/1986 | Lee |
| 4,922,913 A | 5/1990 | Waters, Jr. et al. |
| 5,005,577 A | 4/1991 | Frenkel |
| 5,076,274 A | 12/1991 | Matsumoto |
| 5,109,852 A | 5/1992 | Kaye et al. |
| 5,165,409 A | 11/1992 | Coan |
| 5,179,953 A | 1/1993 | Kursar |
| 5,217,015 A | 6/1993 | Kaye et al. |
| 5,375,595 A | 12/1994 | Sinha et al. |
| 5,636,635 A | 6/1997 | Massie et al. |
| 5,813,982 A * | 9/1998 | Baratta ................ 600/398 |
| 5,830,139 A | 11/1998 | Abreu |
| 6,120,460 A | 9/2000 | Abreu |
| 6,123,668 A | 9/2000 | Abreu |
| 6,213,943 B1 | 4/2001 | Abreu |
| 6,447,449 B1 * | 9/2002 | Fleischman et al. ...... 600/405 |

OTHER PUBLICATIONS

Pending U.S. Fleischman et al. Patent application Ser. No. 09/642,573, filed Aug. 21, 2000 entitled System for Measuring Intraocular Pressure of an Eye and a MEM Sensor for use therewith.

Pending U.S. Fleischman et al. Patent application Ser. No. 10/118,440, filed Apr. 8, 2002 entitled Apparatus and Method for Measuring Intraocular Pressure.

(List continued on next page.)

Primary Examiner—Charles Marmor
(74) Attorney, Agent, or Firm—Tarolli, Sundheim, Covell & Tummino L.L.P.

(57) ABSTRACT

An apparatus for measuring intraocular pressure (IOP) comprises a contact lens including an inner surface contoured to a surface portion of an eye and a sensor disposed in the contact lens. The sensor comprises a contact surface for making contact with the surface portion of the eye. The contact surface includes an outer non-compliant region and an inner compliant region fabricated as an impedance element that varies in impedance as the inner compliant region changes shape. The sensor further comprises a region of conductive material electrically coupled to the impedance element of the compliant region and responsive to an external signal for energizing the impedance element so that the IOP may be determined.

34 Claims, 14 Drawing Sheets

OTHER PUBLICATIONS

Intraocular Pressure Measurement with Instrumented Contact Lenses, Investigative Ophthalmology Report; M. E. Greene, et al.; Apr. 1974, pp. 229–302.

Self–Tonometry to Manage Patients with Glaucoma and Apparently Controlled Intraocular Pressure, J. T. Wilensky, M.D., et al; Arch Ophthalmol, vol. 105, Aug. 1987, pp. 1072–1075.

Passive Radiotelemetry of Intraocular Pressure in Vivo: Calibration and Validation of Continual Scleral Guard–Ring Applanation Transensors in the Dog and Rabbit, R. L. Cooper et al.; Assoc. for Res. in Vis. and Ophthal., Inc., vol. 18, No. 9, Sep. 1979, pp. 930–938.

Continual Monitoring of Intraocular Pressure: Effect of Central Venous Pressure, Respiration, and Eye Movements on Continual Recordings of Intraocular Pressure in the Rabbit, Dog, and Man; R. L. Cooper et al.; British Journal of Ophthalmology, vol. 63, 1979, pp. 799–804.

Radio Telemetry of Intraocular Pressure in Vitro; Cooper et al., Invest. Ophthalmol. Visual Sci. Feb. 1977, pp. 168–171.

Progress in Continual Eye Pressure Monitoring; Cooper et al.; Australian Journal of Ophthalmology, vol. 11, 1983 pp. 143–148.

A New Tonometer Based on the Application of Micro☐Mechanical Sensors, Besten et al.; MESA Research Institute, The Netherlands, 1993, pp. 105–110.

Corneal Bending and Buckling in Tonometry, Marg, Ph.D.; et al.; Archives of Ophthalmology, vol. 4, Jan. 1961, pp. 67–74.

Wireless Micromachined Ceramic Pressure Sensors, Jennifer M. English et al.; School of Electrical and Computer Engineering, Georgia Institute of Technology, IEEE, 1999, pp. 511–516.

Dynamic Tonometry, H. M. Dekking et al.; Ophthalmologica, vol. 154, 1967, pp. 59–75.

A Rapid Pneumatic Applanation Tonometer, Maurice E. Langham, Ph.D. et al.; Arch Ophthal, vol. 79, Apr. 1968, pp. 389–399.

The Validity of the Imbert–Fick Law as Applied to Applanation Tonometry, J. Gloster et al.; Exp. Eye Res., vol. 2, May 1963, pp. 274.283.

The Goldmann Applanation Tonometer, Robert A. Moses, M.D.; pp. 865, 869 (undated).

Magnetic Microactuation of Polysilicon Flexure Structures, Jack W. Judy et al.; 1994, pp. 43–59.

A Theoretical and Experimental Study of the Mechanical Behavior of the Cornea with Application to the Measurement of Intraocular Pressure, Nathan Jay Schwartz et al.; University of California, Berkeley, Bulletin of Mathematical Biophysics, vol. 28, 1966, pp. 585–643.

Intraocular Pressure Changes in Patients with Glaucoma, Moore et al. Moorfields Eye Hospital, London, England, pp. 833–835.

Reliability of Intraocular Pressure Measurements After Myopic Excimer Photorefractive Keratectomy, Abbasoglu, M.D., et al., Ophthalmology, vol. 105, No. 12, Dec. 1998 rev. pp. 2193–2196.

Sources of Error with Use of Goldmann–Type Tonometers, Marc M. Whitacre, M.D., et al.; Survey of Ophthalmology, vol. 38, No. 1, Jul.–Aug. 1993, pp. 1–30.

A Noncontact Applanation Tonometer, Max Forbes, M.D., et al.; Arch Ophthalmol, vol. 91, Feb. 1974, pp. 134–140.

Intraocular Pressure and Tonometry, Edwin M. Schottenstein; Clinical Measurement, Chap. 20, pp. 407–428 (Undated).

Trough Height, Pressure and Flattening in Tonometry, Elwin Marg et al.; Vision Research, vol. 1, 1962, pp. 379–385.

Fast, Automatic, Electronic Tonometers Based on an Exact Theory, R. Stuart Mackay, Ph.D. et al.; Acta Ophthalmologica, vol. 37, 1959, pp. 495.507.

A New Technique for in Vivo Intraocular Pharmacokinetic Measurements, Ocular Dialysis, Joshua Ben–Nun, M.D., et al., Arch. Ophthalmol., vol. 106, Feb. 1988, pp. 254–259.

Diurnal Variation in Intraocular Pressure, Charles D. Phelps, M.D. et al.; American Journal of Ophthalmology, Mar. 1974, pp. 367–376.

A Universal Electromagnetic Microactuator Using Magnetic Interconnection Concepts, Daniel J. Sadler et al.; Journal of Microelectromechanical Systems, vol. 9, No. 4, Dec. 2000, pp. 460–468.

Miniature Passive Pressure Transensor for Implanting in the Eye, Carter C. Collins, IEEE Transactions on Bio–Medical Engineering, vol. BME 14, No. 2, Apr. 1967, pp. 74–83.

\* cited by examiner

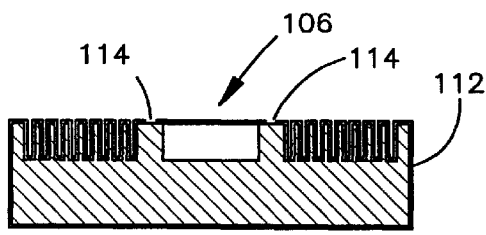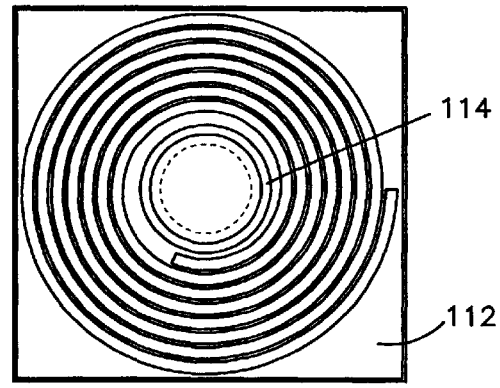
Fig.6(d1)   Fig.6(d2)
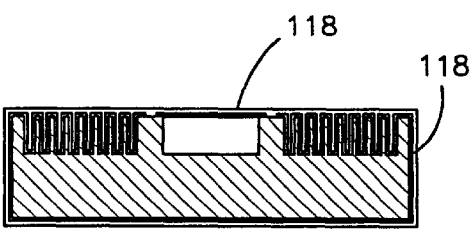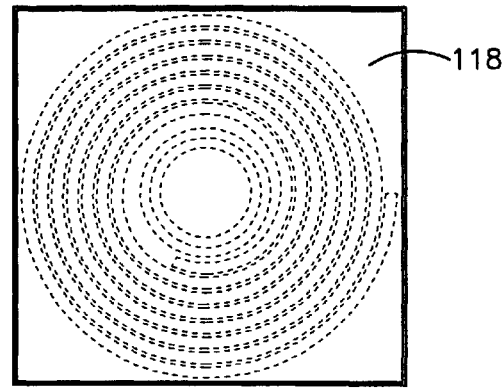
Fig.6(e1)   Fig.6(e2)
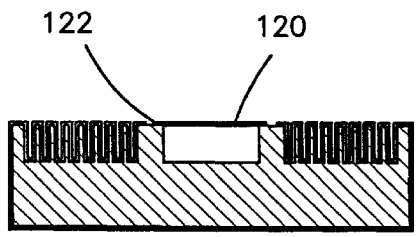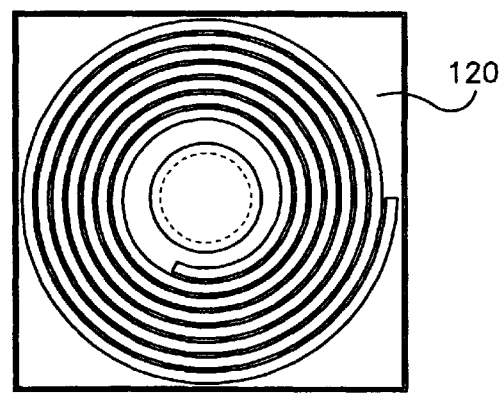
Fig.6(f1)   Fig.6(f2)

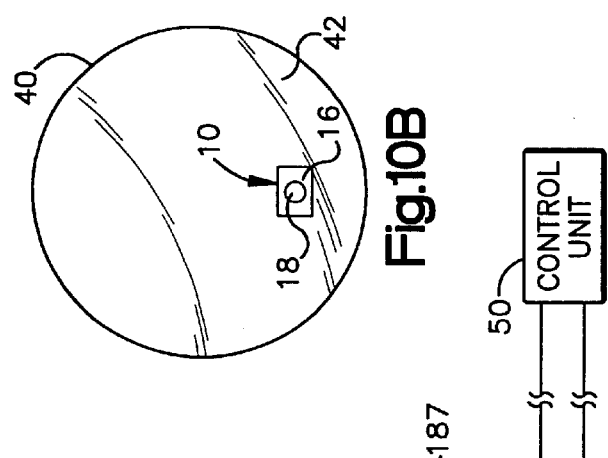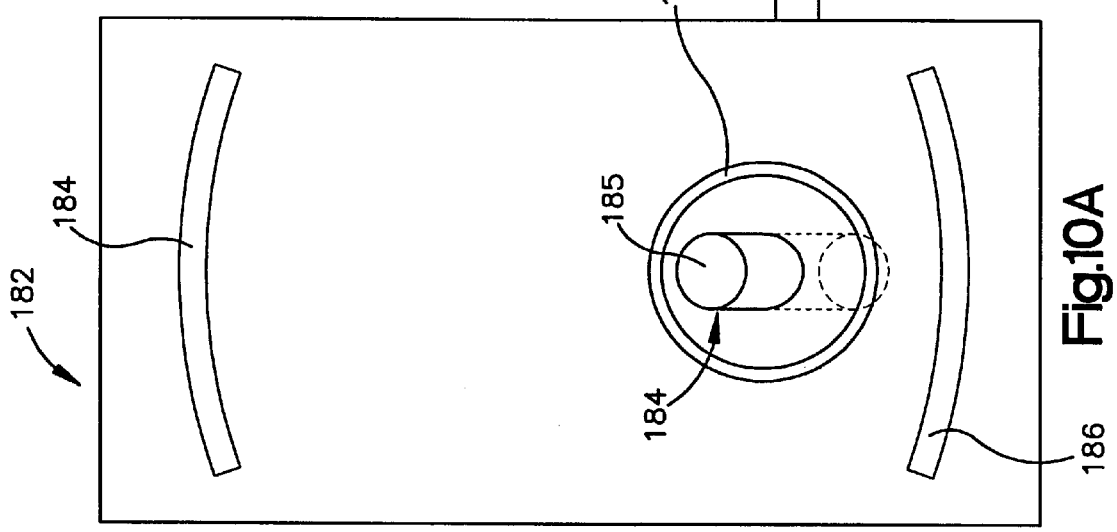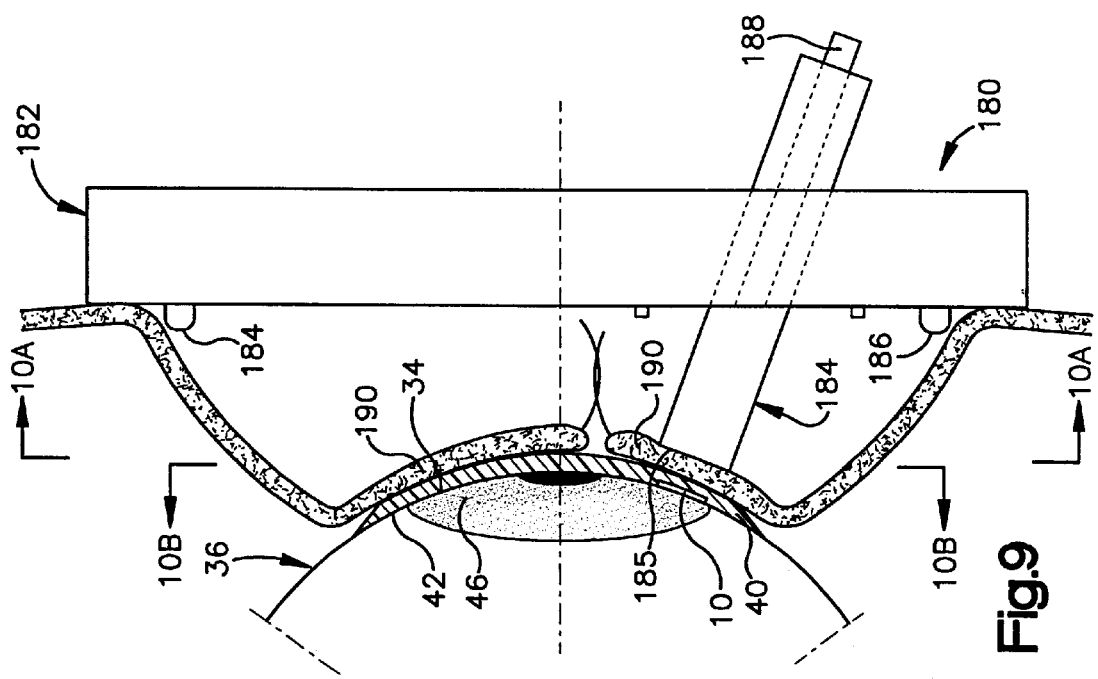

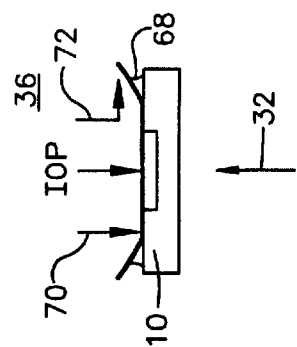
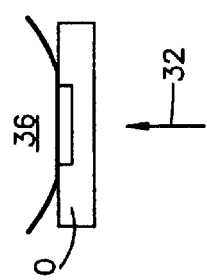
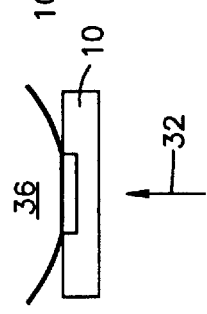
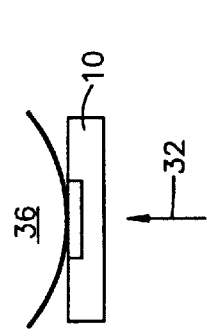
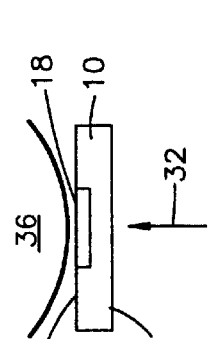
Fig.11(A1) Fig.11(B1) Fig.11(C1) Fig.11(D1) Fig.11(E1)
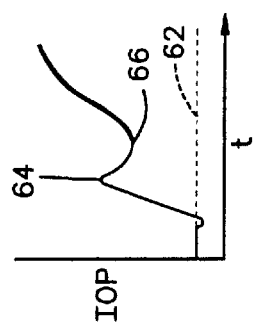
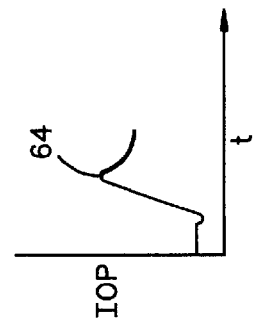
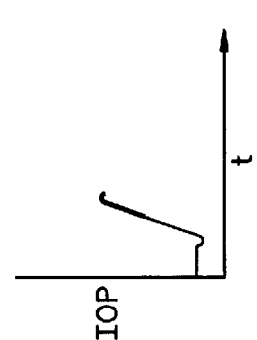
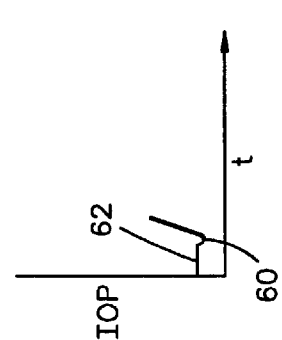
Fig.11(A2) Fig.11(B2) Fig.11(C2) Fig.11(D2) Fig.11(E2)

INTRAOCULAR PRESSURE MEASUREMENT SYSTEM INCLUDING A SENSOR MOUNTED IN A CONTACT LENS

RELATED APPLICATIONS

This application is a continuation-in-part of a co-pending U.S. patent application Ser. No. 09/642,573, entitled "SYSTEM FOR MEASURING INTRAOCULAR PRESSURE FOR AN EYE AND A MEM SENSOR FOR USE THEREWITH", filed Aug. 21, 2000 now U.S. Pat. No. 6,447,449. The subject matter of the aforementioned application is incorporated herein by reference.

FIELD OF THE INVENTION

The present invention relates to a system for measuring intraocular pressure (IOP) in an eye, and is particularly directed to a system for measuring IOP that utilizes a sensor fabricated through microelectromechanical system (MEMS) technology and which is mounted in a contact lens.

BACKGROUND OF THE INVENTION

Glaucoma patients and post-operative patients of eye surgery require regular monitoring of the IOP of their eyes in order to diagnose degenerative conditions which may lead to degraded sight and/or blindness without immediate medical treatment. Accordingly such patients must make frequent trips to their ophthalmologist's office for this regular monitoring of their IOP with conventional mechanical impact type tonometers. This becomes a nuisance to the patient after a time leading to patient resistance to compliance. In addition, the only measurement of the patient's IOP that the doctor can use for diagnosis is the pressure that exists at the time of the office visit. Therefore, if the pressure is normal at the time of the visit, but becomes high thereafter, the patient's actual risk of blindness may be misdiagnosed. Also, if the pressure measured at the time of the office visit is high for reasons other than eye degeneration, the patient may be falsely diagnosed and be required to undergo therapy that may not be needed.

Intraocular pressure has been known to fluctuate widely during any given period of time and thus, should be monitored many times during the period of a day in order to gain an average or representative IOP which in turn may be tracked for diagnosis. Attempts have been made to permit glaucoma patients to monitor their IOP at home many time during the period of a day with a self-tonometry portable instrument. Reference is made to the paper "Self-Tonometry to Manage Patients with Glaucoma and Apparently Controlled Intraocular Pressure", Jacob T. Wilensky et al., published in Arch Ophthalmol, Vol. 105, August 1987 for more details of such a device. This paper describes a portable, tonometer instrument consisting of a pneumatically driven plunger, fitted with an elastic membrane, that slowly comes forward and applanates the cornea. Applanation is detected by an internal optic sensor and the pressure necessary to achieve applanation is registered and displayed automatically. The patient is able to prepare the eye and self-tonometer and activate the instrument for taking the measurement. However, the device proposed is relatively large and bulky, about the size of an attache' case, for example, and not conducive to convenient transport with the patient during normal daily routine in order to measure IOP. In addition, the proposed technique requires special eye preparation by instilling a topical anesthetic in the eye prior to tonometric measurements.

Also, very crude attempts have been made to develop methods of non-invasively monitoring IOP using passive electronic circuitry and radiotelemetry disposed at the eye. In the papers of R. L. Cooper et al. namely, those published in Invest., Ophthalmol Visual Sci., pp. 168–171, February 1977; British JOO, 1979, 63, pp. 799–804; Invest, Ophthalmol Visual Sci., 18, pp. 930–938, September, 1979; and Australian Journal of Ophthalmology 1983, 11, pp. 143–148, a miniature guard ring applanating transsensor (AT) which included electronic components that changed in resonance proportional to the IOP was mounted in an acrylic or sauflon haptic contact lens element that was individually designed for the human eye. The AT was mounted in the lower part of the scleral haptic so that it applanated the inferior sclera under the lower lid. The whole haptic ring was placed in the conjunctival fornix. IOP was monitored from the AT with an automatic continual frequency monitor (ACFM) attached by adhesive and elastic bands to the exterior of the lower eye lid. The ACFM induced in the AT electromagnetic oscillations at varying radio frequencies via a magnetic coupling of inductive coils and monitored for its resonant frequency representative of IOP. This device is clearly uncomfortable and bulky, minimizing expected patient compliance. In addition, the device measures IOP by applanation of the sclera, which is a rather unconventional method of measuring IOP.

In another paper reported in Investigative Ophthalmology Reports, pp. 299–302, April, 1974 by B. G. Gilman, a device is presented for measuring IOP of a rabbit in a continuous manner with strain gauges mounted (embedded) in soft flush fitting, silastic gel (hydrogel) contact lenses. The exact shape of the eye of the rabbit was obtained by a molding procedure. Leads of the strain gauges extended from the lens and were connected to a wheatstone bridge arrangement for measurement taking. The paper suggests that the embedded strain gauges may be used with a miniature telemetry package completely contained in a hydrophilic hydrogel contact lens for continuous, noninvasive, long duration monitoring of IOP, although no design was provided. This device proposes wire connections for telemetry which entails wires to be run out of the eye under the eyelid. Also, the proposed approach requires the molding of a special contact for each individual eye, a practice which would make widespread use unattractive and expensive.

In 1993, an IEEE paper was presented by C. den Besten and P. Bergveld of the University of Twente, The Netherlands, proposing a new instrument for measuring area of applanation entitled "A New Tonometer Based on Application of Micro-Mechanical Sensors". This new instrument is based on the Mackay-Marg principle of tonometer operation in which a plate having a diameter of 6 mm or less is pressed against and flattens a portion of the cornea of the eye, referred to as "applanation". In the middle of the plate is a small pressure sensitive area that is pressed against the flattened portion of the cornea with a slowing increasing force while the pressure area is electronically measured. The applanation sensor of this new instrument comprises a micro-machined plunger and pressure sensing electronics on three electrically insulated levels of a silicon substrate resulting in a modified Mackay-Marg tonometer in which the radius of the flattened area and the distance between the periphery of the applanation and the pressure center can be measured to render a more accurate pressure area measurement. In the work presented in this paper, the researchers did not actually propose a pressure sensor or transducer. In addition, it is not clear if, for as long as the eye is applanated, there is a need to know the area of applanation. Sufficient applanation is usually determined by the difference in trough height from the peak to dip of the pressure profile. The dip is unlikely to occur unless sufficient applanation is achieved.

Also, in the U.S. Pat. No. 5,830,139 entitled "Tonometer System for Measuring Intraocular Pressure by Applanation and/or Indentations", issued to Abreu on Nov. 3, 1998, a tonometer system is disclosed using a contact device shaped to match the outer surface of the cornea and having a hole through which a movable central piece is slidably disposed for flattening or indenting a portion of the cornea. A magnetic field controls the movement of the central piece against the eye surface to achieve a predetermined amount of applanation. A sophisticated optical arrangement is used to detect when the predetermined amount of applanation has been achieved to measure IOP and a calculation unit determines the intraocular pressure based on the amount of force the contact device must apply against the cornea in order to achieve the predetermined amount of applanation. The magnetic and optical arrangements of this device requires special alignment and calibration techniques rendering it difficult for use as a self-tonometry device.

While the various foregoing described U.S. patent and papers propose various devices and instruments for tonometry, none appears to offer a viable inexpensive, convenient solution to the immediate problem of self-tonometry. The present invention overcomes the drawbacks of the proposed instruments described above to yield a simple, inexpensive and easy to use instrument that completely automates the tonometry process and offers post-processing of tonometer IOP readings from which a proper elevation and diagnosis by an ophthalmologist may be performed.

SUMMARY OF THE INVENTION

The present invention is an apparatus for measuring intraocular pressure of an eye. The apparatus comprises a contact lens including an inner surface contoured to a surface portion of the eye and a sensor disposed in the inner surface of the contact lens. The sensor comprises a contact surface for making contact with the surface portion of the eye. The contact surface includes an outer non-compliant region and an inner compliant region fabricated as an impedance element that varies in impedance as the inner compliant region changes shape. The sensor further comprises a region of conductive material that is electrically coupled to the impedance element of the compliant region and responsive to an external signal for energizing the impedance element so that the intraocular pressure may be determined.

The present invention also provides a method for measuring intraocular pressure (IOP) of an eye. According to the inventive method, a contact lens is provided with an inner surface contoured to the eye. The contact lens includes a sensor disposed in the inner surface of the contact lens. The sensor has a compliant region that functions as an impedance element. The contact lens is positioned on the surface portion of the eye. An applanator is provided for applying pressure against the contact lens. The applanator is moved toward the eye until the sensor forcefully engages the surface portion of the eye which causes the compliant region to change shape and vary in impedance. The impedance element is energized and a representative pressure measurement is determined each time the impedance element is energized. The representative pressure measurements are processed to render a resultant IOP measurement.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 9 is a side illustration of an apparatus for measuring IOP of an eye using the tonometer sensor of FIG. 3;

FIG. 10A is a sectional view taken along line 10A—10A in FIG. 9 with parts omitted for clarity;

FIG. 10B is a sectional view taken along line 10B—10B in FIG. 9 with parts omitted for clarity;

FIGS. 11A1—11E2 are illustrations of the response of the apparatus of FIG. 9 to contact with an eye;

DETAILED DESCRIPTION OF EMBODIMENTS

Figure 1:
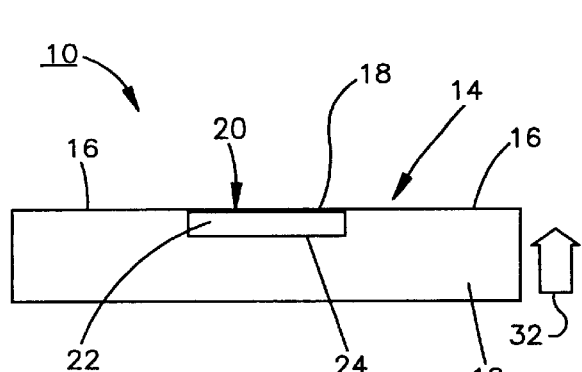
FIG. 1 is a cross-sectional view of a first embodiment of a tonometer sensor for use in the present invention.
Figure 2:
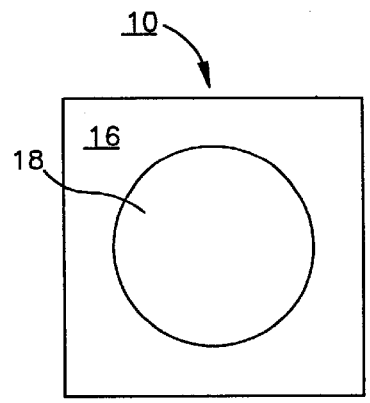
FIG. 2 is a plan view of the tonometer sensor of FIG. 1.

A tonometer sensor 10 produced using microelectromechanical system (MEMS) techniques is shown in FIGS. 1 and 2. The tonometer sensor 10 includes a substrate 12 that is comprised of a silicon material, but it should be understood that other materials may be used. The substrate 12 includes a contact surface 14 for making contact with a surface portion 34 (FIG. 3A) of an eye 36. The contact surface 14 includes an outer non-compliant region 16 (FIG. 1) and an inner compliant region 18 that is fabricated using MEMS techniques (which will be described in greater detail herein below) as an impedance element, the impedance of which varies as the inner compliant region 18 changes shape. The compliant region 18 comprises a diaphragm 20 as one plate of a capacitive element that is separated by a dielectric 22 from another plate 24 of the capacitive element which is part of the non-compliant region 16. As will become more evident from the description below, as the contact surface 14 is pressed against the surface portion of the eye, the diaphragm plate 20 flexes closer to the other non-compliant plate 24 to change the capacitance of the capacitive element in proportion to the intraocular pressure (IOP) of the eye. In the illustrated embodiment, the dielectric comprises air, but other suitably compliant dielectrics such as hydrogel and silicone, for example, may also be used, without deviating from the principles of the present invention.

Figure 3A:
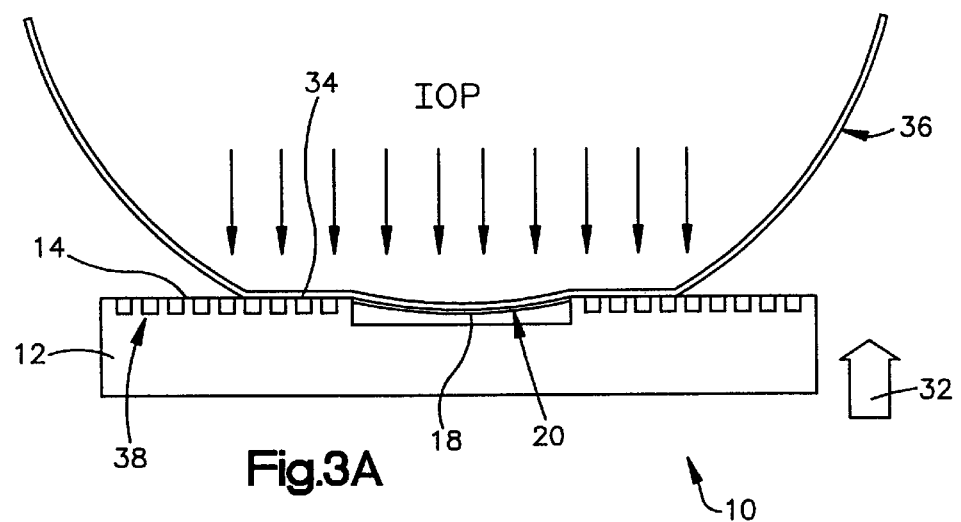
FIGS. 3A and 3B are cross-sectional and plan views, respectively, of the tonometer sensor illustrating additional regions in accordance with the present invention.
Figure 3B:
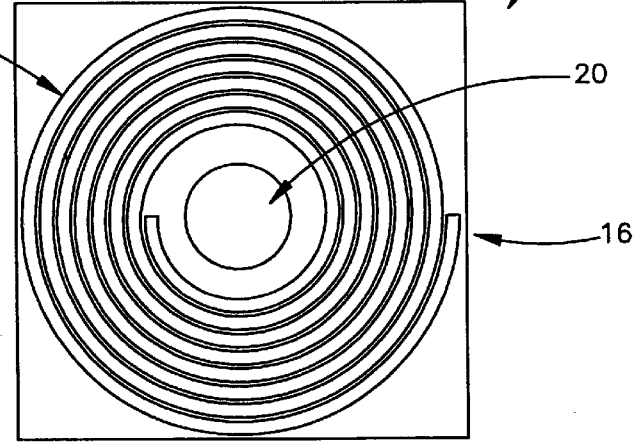

As shown by the substrate cross-sectional and plan views of FIGS. 3A and 3B, respectively, a region of conductive material 38 is included as part of the substrate 12 and is electrically coupled to the impedance element of the compliant region 18 (diaphragm 20) which is a capacitive element. While not shown in FIGS. 3A and 3B, this electrical coupling is described in greater detail in connection with the fabrication drawings found herein below. The conductive material 38 is responsive to an external signal for energizing the impedance element so that the IOP may be determined. In FIGS. 3A and 3B, the conductive region 38 comprises an inductor coil fabricated in the non-compliant region 16 of the contact surface 14 such that it is electrically coupled to the capacitive element to form a resonance or tank circuit. It should be understood that other types of sensors (piezoelectric, piezoresistive, strain-gage based, etc.) could be substituted for the sensor 10. Such other types of sensors would likely require use of other known telemetry techniques rather than a tank circuit.

Figure 4A:
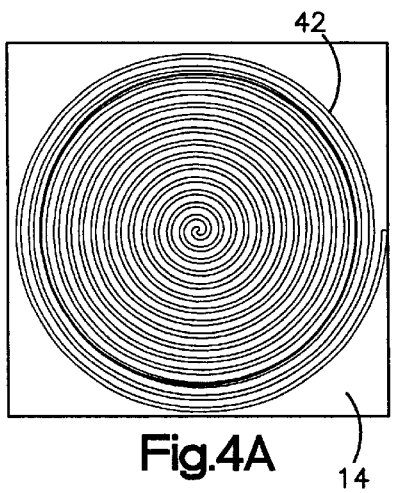
FIGS. 4A and 4B are cross-sectional and plan views, respectively, of a tonometer sensor constructed in accordance with an alternate embodiment of the present invention.
Figure 4B:
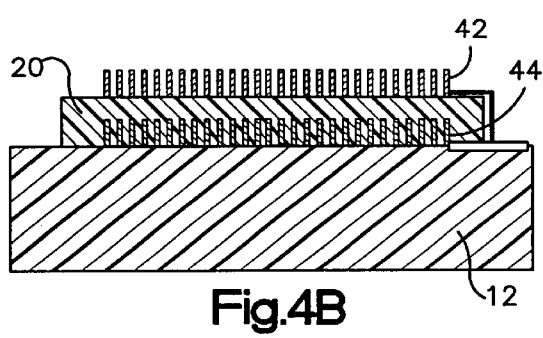

In the present embodiment, the inductor coil 38 is formed by disposing conductive material in a predetermined pattern, like a concentric spiraled pattern, for example, in the non-compliant region 16. A process for fabricating the inductor coil 38 at the non-compliant region 16 is described in greater detail herein below. However, it should be understood that the inductor region need not be embodied solely at the non-compliant region 16 and may be embodied as part of the compliant region 18 as well without deviating from the principles of the present invention. Further, it should be understood by those of ordinary skill in the art that there could be a spiral inductor 42 on the contact surface 14 of the diaphragm 20 coupled to a flat spiral inductor 44 underneath the diaphragm as illustrated in the alternate embodiment of FIGS. 4A and 4B. Yet another alternative would include a combination of the aforementioned spiral inductor 42 and the capacitive element, formed by the diaphragm (plate) 20 and the fixed plate 24, acting in conjunction with each other, meaning the inductance and the capacitance will increase (as the plates get closer to each other) or decrease together.

In the present embodiment, the resonant circuit comprising the inductor coil 38 and the capacitive element formed by the plates 20 and 24 may be excited into resonance by an external electromagnetic signal in the radio frequency (RF) range. Tank circuits of this type have a natural resonant frequency fo that, to the first order, depends of the values of the inductor and the capacitor as follows:

$$fo = \frac{1}{2\pi(LC)^{1/2}}$$

where L is the inductance and C is the capacitance. Accordingly, as the capacitance of the tonometer sensor 10 changes, the resonant frequency fo of the tank circuit will change in proportion thereto.

For example, if the contact area 14 of the tonometer sensor 10 is approximately one square millimeter (1 mm$^2$) or one millimeter (1 mm) on each side, the diaphragm 20 of the compliant region 18 may have a diameter of five hundred micrometers (500 $\mu$m) with a one and a half micrometer (1.5 $\mu$m) dielectric or air gap, and the inductor coil may have twenty-five (25) turns with an inside diameter (ID) of five hundred micrometers (500 $\mu$m) and an outside diameter (OD) of one thousand micrometers (1,000 $\mu$m) With the diaphragm 20 undisturbed, the resonant frequency may be on the order of one hundred and ninety-three megahertz (193 MHz). Accordingly, a ten percent (10%) increase in capacitance, for example, resulting from a diaphragm 20 deflection will produce a downward shift in resonant frequency to one hundred and eighty-four point one megahertz (184.1 MHz) and this shift in resonant frequency is readily discernible electronically as will be further described herein below. It is understood that the contact area of the sensor 10 may be less than 1 mm, in which case the various dimensions may be rescaled proportionately.

Figure 5A:
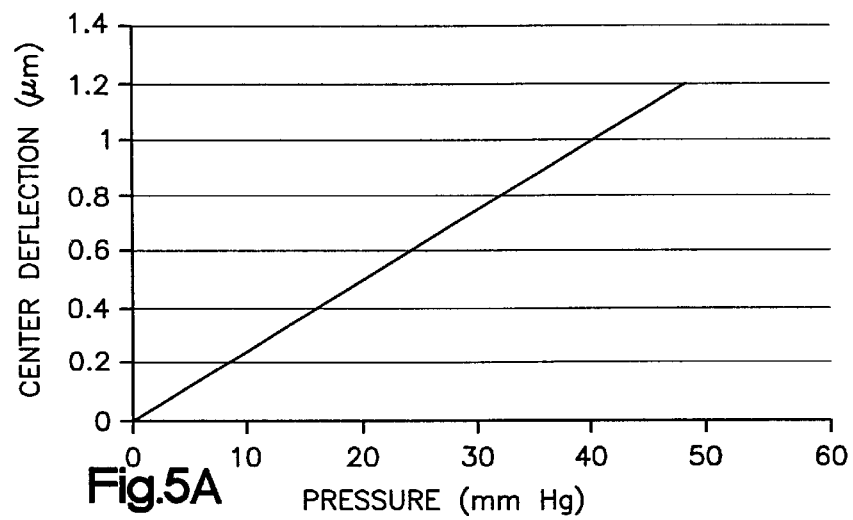
FIG. 5A is a graph illustrating the relationship between deflection of the tonometer sensor and intraocular pressure (IOP)
Figure 5B:
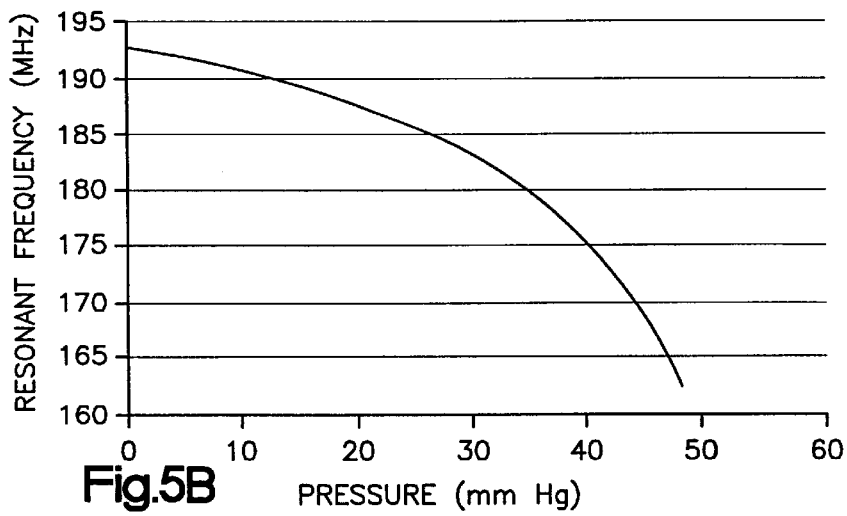
FIG. 5B is a graph illustrating the relationship between resonant frequency of the tonometer sensor and IOP.

As has been described in connection with the illustration of FIG. 3A, the deflection of the diaphragm 20 of the compliant region 18 as the contact surface 14 of the substrate 12 is pressed against the surface portion 34 of the eye 36 is representative of the IOP of the eye. The graph of FIG. 5A illustrates an exemplary center deflection in micrometers ($\mu$m) expected for a diaphragm 20 with the geometry described above as a function of the IOP of the eye expressed in parametric units of millimeters of Mercury (mm Hg). It is this deflection of the diaphragm 20 which causes the change in capacitance and may be measured by the resultant change in resonant frequency of the tank circuit. The graph of FIG. 5B illustrates an estimated change in resonant frequency based upon a conservative approximation of a corresponding change in capacitance resulting from the deflection of the diaphragm 20 due to IOP. The expression of resonant frequency (MHz) to IOP (mm Hg) illustrated by the graph is nonlinear as expected in a capacitive sensing structure for measuring IOP.

Figure 6:
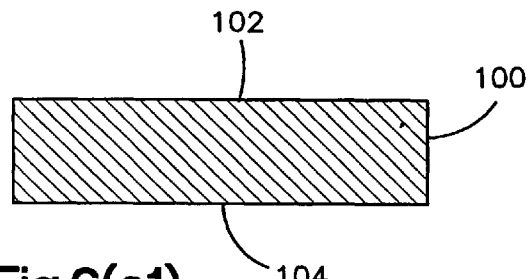
FIGS. 6(a1)–6(i2) are cross-sectional and plan views, respectively, of the tonometer sensor through various stages of a fabrication process.
Figure 6:
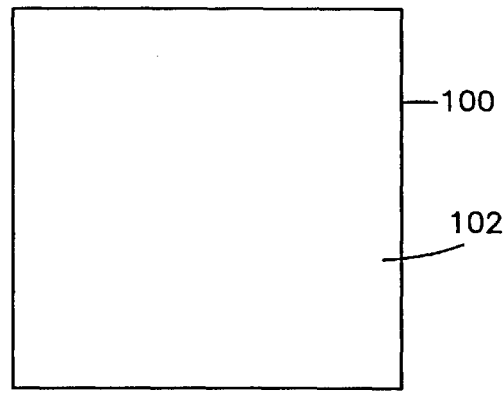
Figure 6:
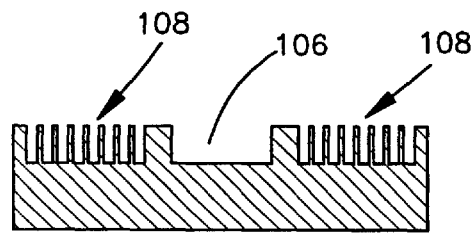
Figure 6:
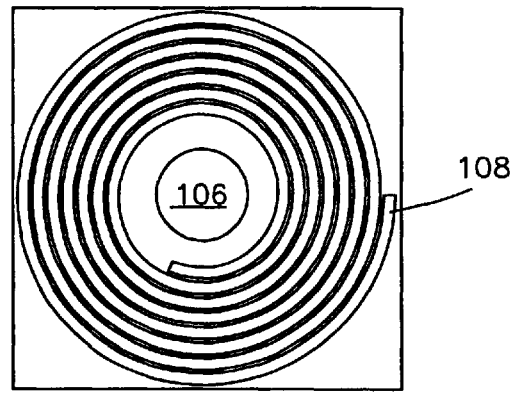
Figure 6:
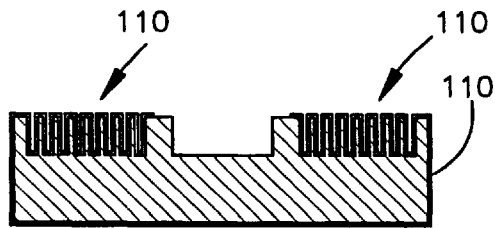
Figure 6:
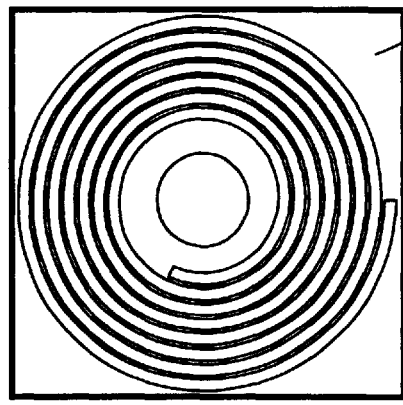
Figure 6:
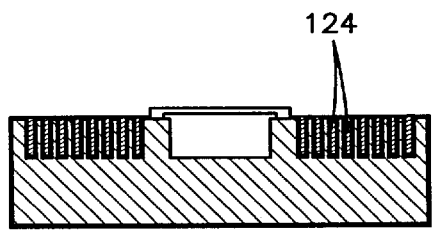
Figure 6:
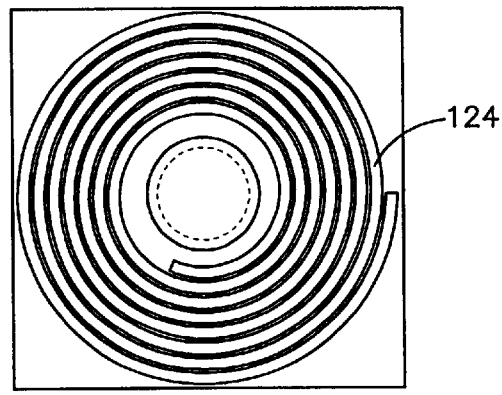
Figure 6:
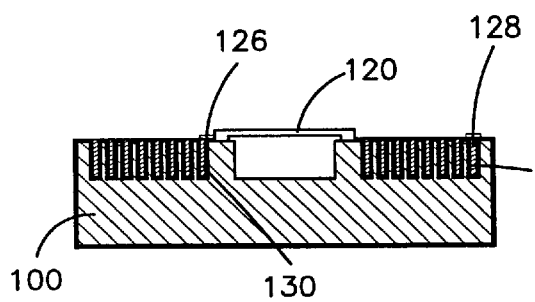
Figure 6:
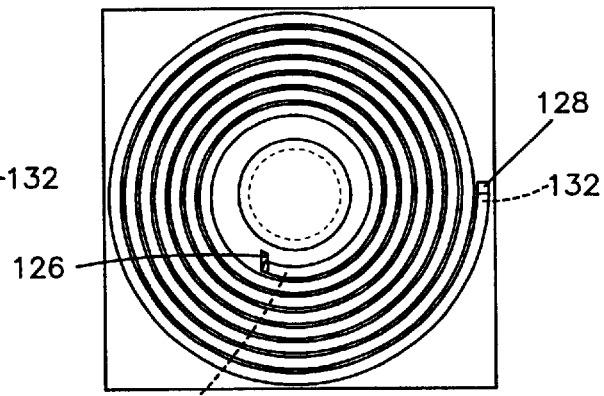
Figure 6:
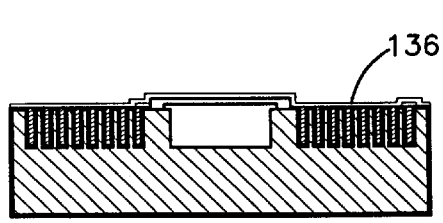
Figure 6:
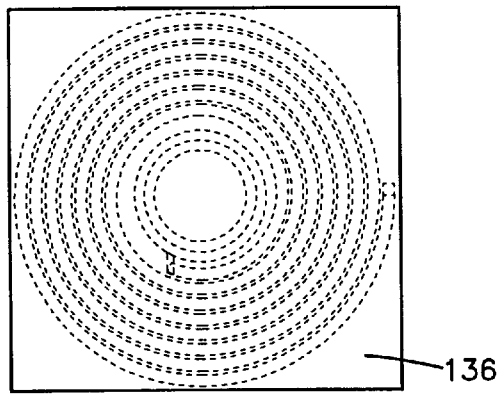

An exemplary process suitable for fabricating an embodiment of the tonometer sensor 10 is shown in the process diagrams of FIGS. 6(a1) through 6(i2) wherein each Figure provides cross-sectional and plan views, respectively, of the sensor structure at various stages of the fabrication process. The process starts with a substrate 100 which may be part of a silicon wafer, for example, as shown in FIG. 6(a). It is understood that materials other than silicon may be used for the substrate in which case the process may be slightly modified to accommodate such other material. The substrate has a top surface 102 and a bottom surface 104. In the step of FIG. 6(b), an etch resistant layer is provided over the substrate, like silicon dioxide (SiO$_2$), for example, and the top surface 102 is patterned using conventional lithograph/etching processes to form the capacitor well region 106 having a diameter of approximately 500 $\mu$m, for example, and spiraled groove regions 108 of a width on the order of 5 $\mu$m, for example, for the inductor coil. Thereafter, the unpatterned etch resist areas of the Si substrate are etched using a deep etch process, like reactive ion etching, for example, to a depth of one to twenty microns and the etch resist is removed rendering a structure as shown in FIG. 6(b).

In the step of FIG. 6(c), a layer of silicon nitride (Si$_3$N$_4$) or other similar material 110 is deposited on the surfaces of the substrate 100. A conformal coating of Si$_3$N$_4$ is deposited over the surface of the substrate through a conventional chemical vapor deposition (CVD) process to a thickness of approximately 1200 Å–2400 Å, for example. Next, in the step of FIG. 6(d), a layer of low temperature oxide (LTO) 112 is deposited over the Si$_3$N$_4$ layer 110 by conventional CVD to a thickness of approximately 2–3 $\mu$m, for example. The LTO layer 112 of the top surface 102 is polished smooth using a chemical mechanical polishing process, for example, and patterned using a conventional photolithography process to form an anchor region 114 which, for the present embodiment, is in the form of an annulus of a width of approximately 50–100 microns surrounding the capacitive well region 106. The anchor region 114 is etched through the LTO layer 112 down to the $Si_3N_4$ layer 110 using a reactive ion etching process, or a wet etching process using buffered hydrofluoric acid (BHF), or other similar process.

In the step of FIG. 6(e), a layer of polysilicon 118 is deposited, preferably by CVD, over the surface of the LTO layer 112 of FIG. 6(d) and the layer of polysilicon at the top surface 102 is patterned and etched in a conventional manner to form an unetched layer of polysilicon 120 covering substantially the capacitive well region 106 and anchored by region 114 to the nitride layer. A hole 122 may be provided through an edge of the polysilicon layer 120 to the LTO and $Si_3N_4$ layers 112 and 110 thereunder by the aforementioned patterning and etching process of FIG. 6(e). A post annealing process is performed to render the membrane section of polysilicon 120 in tension. In the present embodiment, the structure of FIG. 6(f) is put in an oven and heated for approximately 30 minutes at approximately 900° C. which changes the crystalline makeup of the polysilicon to provide for stress modification thereof.

In the step of FIG. 6(f), the LTO and nitride layers 112 and 110, including the layers under the polysilicon layer 120, are removed, preferably by a conventional BHF etching process wherein the BHF is allowed to flow through the hole 122 and etch the LTO and nitride layers under the polysilicon layer 120 which are released in solution through the same hole 122. Accordingly, a polysilicon diaphragm 120 in tension is produced as shown in FIG. 6(f). Next, the hole 122 in the polysilicon diaphragm is sealed by growing a low temperature oxide layer (not shown) over the hole 122 in a conventional furnace environment.

In the step of FIG. 6(g), the grooved areas 108 may be pretreated to accept a conductive material which may be deposited in the grooves by conventional plating, sputtering or evaporation techniques, for example, to form the inductor coil 124. Metals which may be used for this process include Ni, Au, Fe, Ag, and Pt to name a few. Preferably, the metallic plating is performed electroless, but electroplating may also be used without deviating from the principles of the present invention.

As shown in FIG. 6(h), interconnects 126 and 128 are provided from the ends of the inductor coil 124 to corresponding sides of the capacitive element. For the interconnect region 126, a window is formed in the nitride layer 110 between the conductive material of the inside coil 130 and the polysilicon layer 120 which is one side of the capacitive element of the sensor 10. When the window region is plated, the metal end 130 of the inductor coil 124 will make electrical contact with one side 120 of the capacitive element. For the interconnection region 128, a window is formed in the nitride layer 110 between the substrate and the groove of the other end 132 of the coil 124 such that when plated, metal electrically connects the other end 132 of the coil 124 with the silicon substrate 100, which is the other side of the capacitive element, thus, completing the tank or oscillatory circuit. In the step of FIG. 6(i), a thin layer of non-conducting material 136 may be grown over the metallic plated surfaces of the non-compliant region 16 to ensure against the sections of the inductor coil 124 making contact with each other over the surface of the nitride layer 110.

Figure 7:
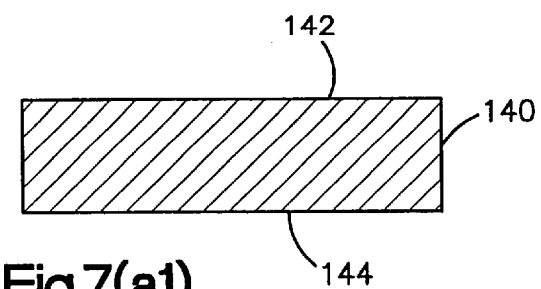
FIGS. 7(a1)–7(j2) are cross-sectional and plan views, respectively, of an alternate tonometer sensor through various stages of a fabrication process.
Figure 7:
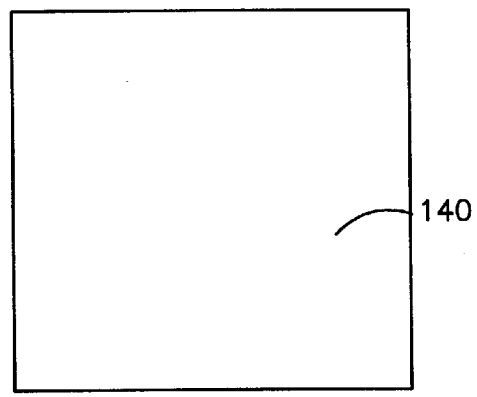
Figure 7:
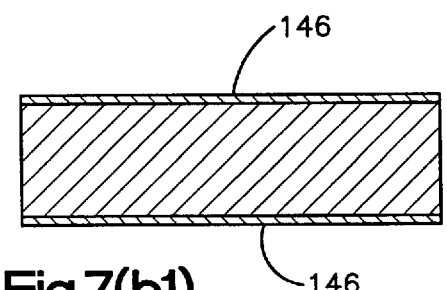
Figure 7:
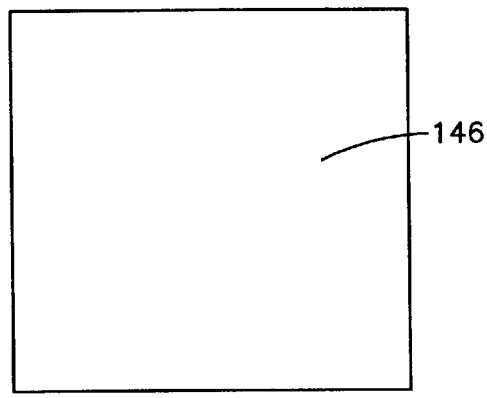
Figure 7:
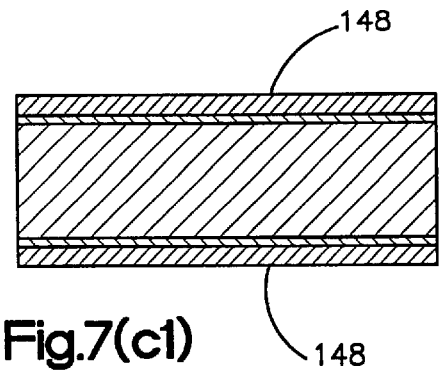
Figure 7:
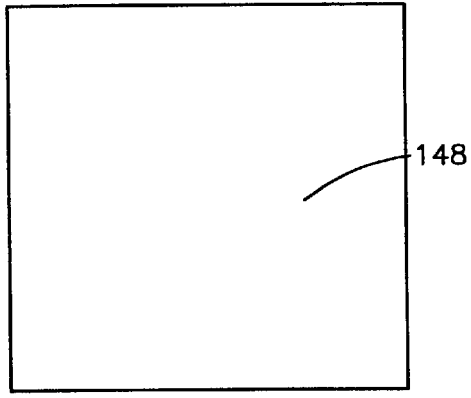
Figure 7:
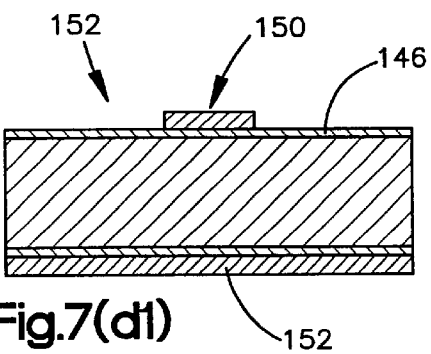
Figure 7:
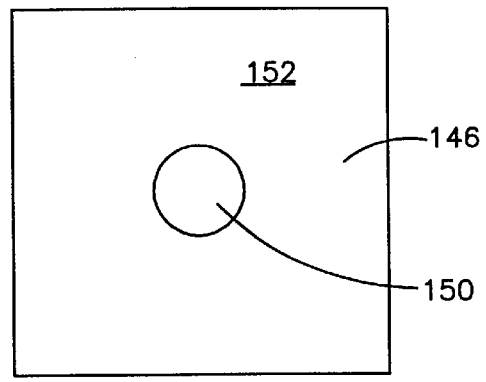
Figure 7:
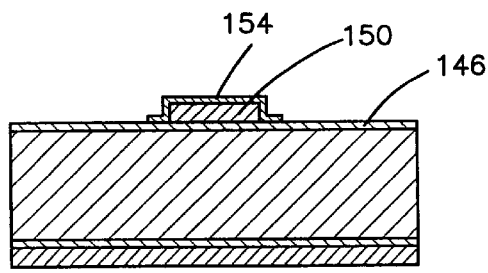
Figure 7:
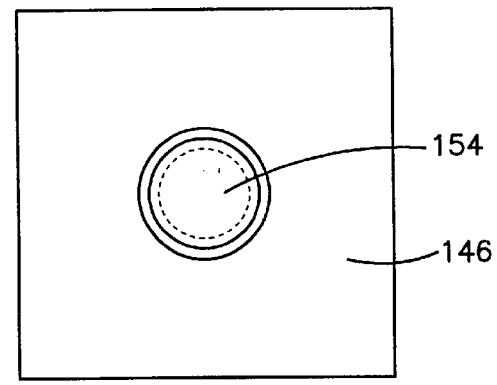
Figure 7:
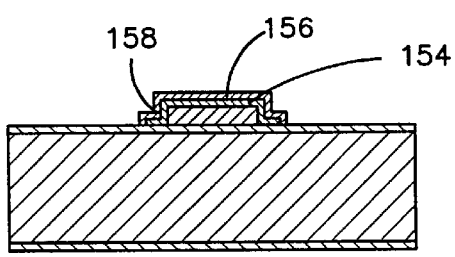
Figure 7:
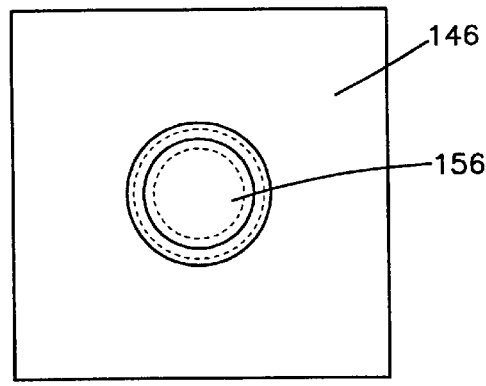
Figure 7:
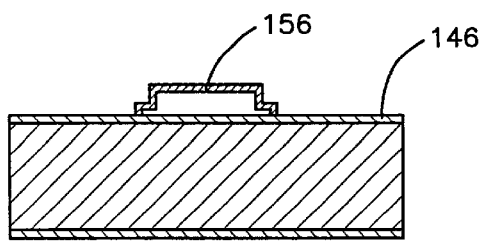
Figure 7:
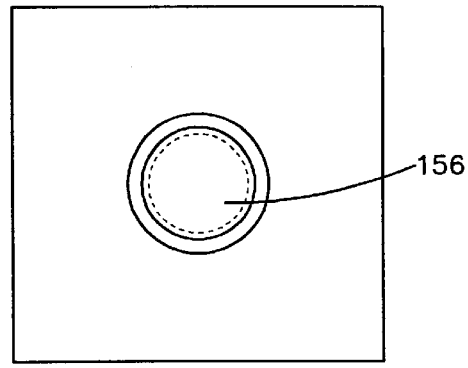
Figure 7:
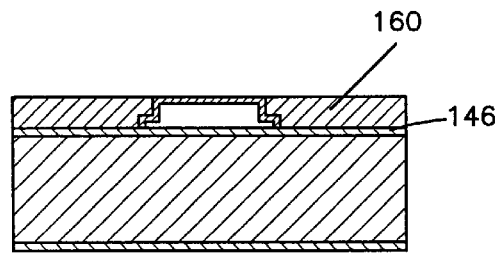
Figure 7:
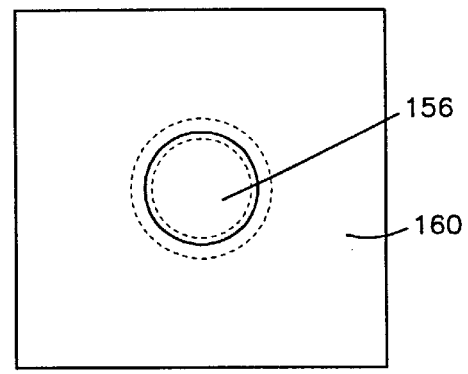
Figure 7:
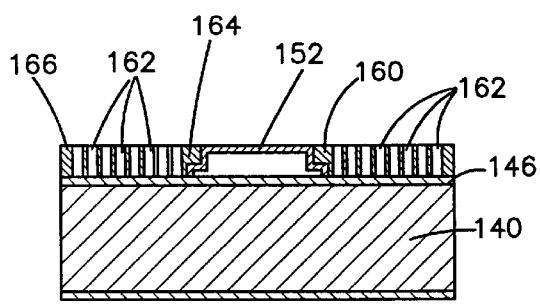
Figure 7:
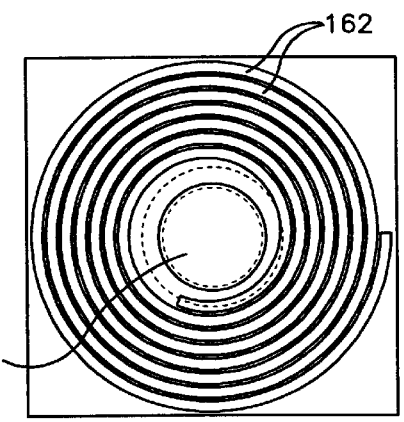
Figure 7:
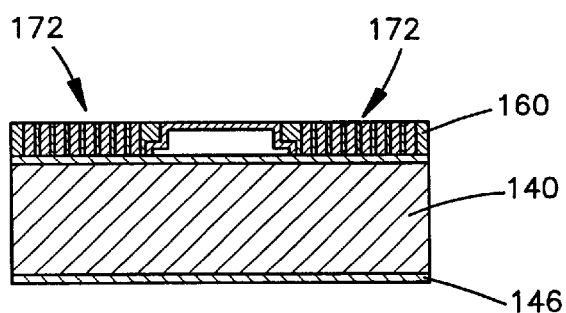
Figure 7:
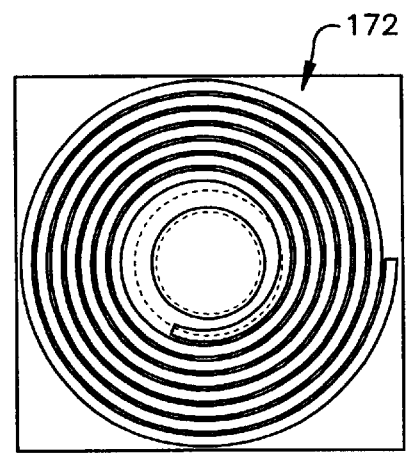

An embodiment for illustrating a fabrication process of an alternate embodiment of the tonometer sensor 10 is shown in the FIGS. 7(a1) through 7(j2) wherein each Figure provides cross-sectional and plan views, respectively, of the alternate sensor structure at various stages of the fabrication process. The process starts with a substrate 140 which may be part of a silicon wafer, for example, as shown in FIG. 7(a). It is understood that materials other than silicon may be used for the substrate in which case the process may be slightly modified to accommodate such other material. The substrate 140 has a top surface 142 and a bottom surface 144. In the step of FIG. 7(b), a layer of silicon nitride ($Si_3N_4$) or other similar material 146 is deposited on the top and bottom surfaces 142 and 144 of the substrate 140. In the present embodiment, the $Si_3N_4$ 146 is deposited through a conventional chemical vapor deposition (CVD) process to a thickness of approximately 1200 Å, for example.

Next, in the step of FIG. 7(c), a layer of low temperature oxide (LTO) 148 is deposited over the $Si_3N_4$ layer 146 by conventional CVD to a thickness of approximately 1.5 µm, for example. The LTO layer 148 of the top surface 142 is patterned using a conventional photolithography process to form a circled region 150 having a diameter of approximately 500 µm, for example, on top of the $Si_3N_4$ layer 146, and the unpatterned regions 152 around the circled region 150 and on the bottom surface 144 are etched using a reactive ion etching process or a wet etching process using buffered hydrofluoric acid (BHF), or other similar process.

The top surface 142 of the resulting structure as shown in FIG. 7(d) is deposited with another low temperature oxide layer, preferably by CVD, to a thickness of approximately 0.5 µm, for example. This second LTO layer 154 is patterned and etched in a conventional manner such that the remaining unetched second LTO layer overlaps the circled layer 150 concentrically to form an annular region of approximately 50 µm on top of the $Si_3N_4$ layer 146 surrounding the circled region 150 as shown in FIG. 7(e).

In the step of FIG. 7(f), a layer of polysilicon is deposited, preferably by CVD, over the top surface 142 of the structure of FIG. 7(e), and the layer of polysilicon is patterned and etched in a conventional manner to form an unetched layer of polysilicon 156 covering substantially the second LTO layer 154. A hole 158 may be provided through the polysilicon layer 156 to the LTO layers 150, 154 thereunder by the aforementioned patterning and etching process of FIG. 7(f). A post annealing process is performed to render the membrane section of polysilicon 156 in tension. In the present embodiment, the structure of FIG. 7(f) is put in an oven and heated for approximately 30 minutes at approximately 900° C. which changes the crystalline makeup of the polysilicon to provide for stress modification thereof.

In the step of FIG. 7(g), the LTO layers 150 and 154 under the polysilicon layer 156 are removed by a conventional BHF etching process wherein the BHF is allowed to flow through the hole 158 and etch the LTO layers under the polysilicon layer 156 which are released in solution through the same hole 158. Accordingly, a polysilicon diaphragm 156 in tension is produced. Next, the hole 158 in the polysilicon diaphragm is sealed by growing a low temperature oxide layer over the hole in a conventional furnace environment.

Next, in the step of FIG. 7(h), a polymer layer 160 which may be a photosensitive polyimide, a photoresist material, PMMA, or the like, is deposited over the $Si_3N_4$ layer 146 of the top surface 142. Patterning of the polymer layer depends on the type of polymer used. For example, if a polyimide is used, conventional photolithography may be used to form the annular winding pattern of the inductor coil 124. The patterned portions of the polyimide are etched conventionally down to the $Si_3N_4$ layer 146 to provide grooves 162 in which to plate the metallic material of the inductor coil 124 within the polyimide layer 160 on the $Si_3N_4$ layer 146 as shown in FIG. 7(i). Preferably, the metallic plating is performed electroless, but electroplating may also be used without deviating from the principles of the present invention. One groove 164 in the polyimide layer 160 goes down to the annulus of the polysilicon layer 156 so that when plated, the metal end of the inductor coil 124 will make contact with the polysilicon 156 which is one side of the capacitive element of the sensor 10. In addition, a hole may be provided through the $Si_3N_4$ layer 146 at the groove 166 of the other end of the inductor coil 124 to allow the plated metal in the groove 166 to pass through the hole and make contact with the silicon substrate 140, which is the other side of the capacitive element, thus completing the tank or oscillatory circuit. As shown in FIG. 7(*j*), a thin layer of non-conducting material may be grown over the metallic plated surfaces 172 of a non-compliant region to ensure against the sections of coil making contact with each other over the surface of the polyimide layer 160.

Figure 8:
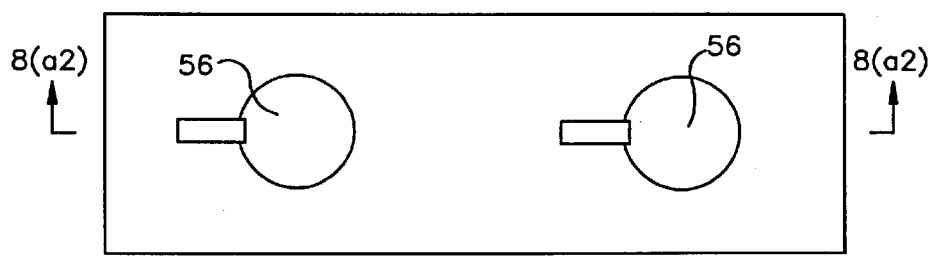
FIGS. 8(a1)–8(d) are cross-sectional and plan views of another alternate tonometer sensor through various stages of a fabrication process.
Figure 8:
Figure 8:
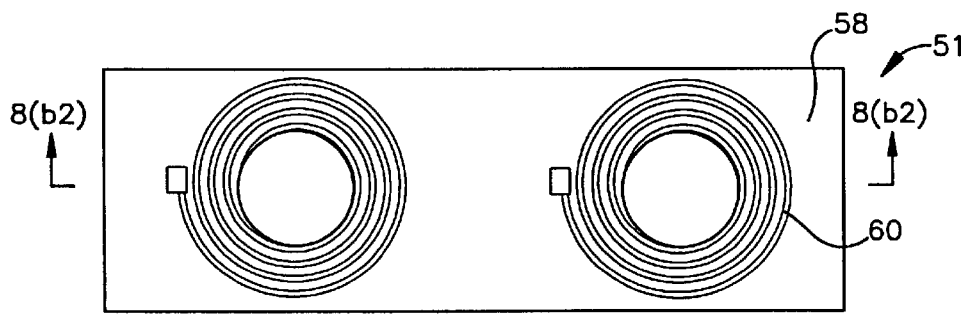
Figure 8:
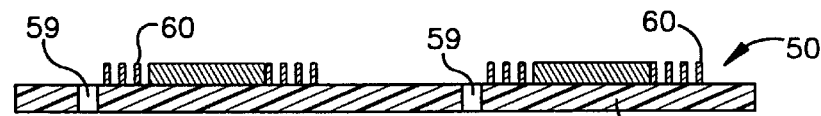
Figure 8C:
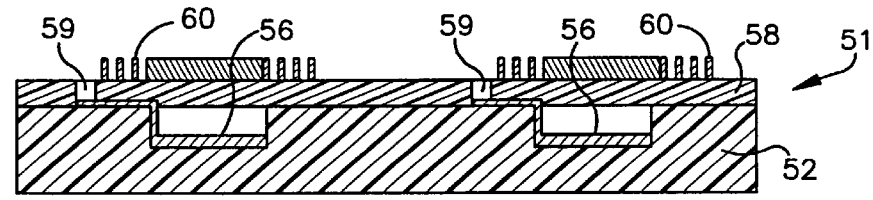
Figure 8D:
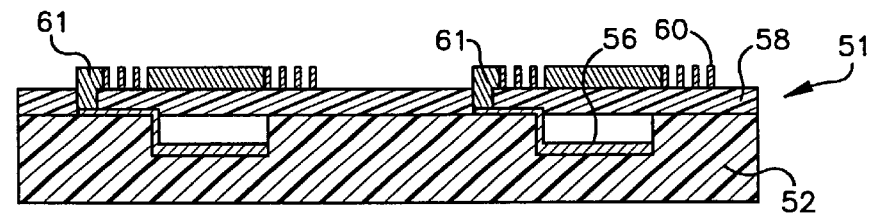

While the present MEMS sensor 51 is described as being fabricated on a silicon substrate, it is understood that other substrates may be used such as a polymeric material, including plastics and polymer films, for example. Such an alternate MEMS sensor 51 could be fabricated using a well-known micro-replication process such as is illustrated in FIGS. 8(*a*)–8(*d*), with the simultaneous fabrication of two of the sensors 51 being shown side by side. In FIGS. 8(*a*1) and 8(*a*2), a thin film of plastic or polymer is mechanically patterned, preferably with dimples that would represent wells 54, by a conventional process. The film 52 would then be metalized to form a ground electrode 56. A second film 58 (FIG. 8(*b*1) could be metalized in a pattern to form an inductor 60 and capacitor (tank circuit). The two films 52 and 58 are then aligned and ultrasonically bonded together. Following a final metallization step (FIG. 8(*d*)) in which a metal is passed through a hole 59 in the second film 58 to form interconnecting conductors 61, the tonometer sensor 51 has a structure similar to the structures described herein above for a silicon substrate, but made from a plastic or polymer film instead.

Referring now to FIG. 9, an apparatus 180 that uses the sensor 10 to measure IOP is illustrated. The apparatus 180 comprises a contact lens 40 having an inner surface 42 contoured to the surface portion 34 of the eye 36. The contact lens 40 may be made of hydrogel or other suitable material. The sensor 10 is disposed in the inner surface 42 of the contact lens 40 so that the contact surface 14 faces the surface portion 34 of the eye 36. FIG. 10B illustrates that the sensor 10 is mounted off-center in the contact lens 40. The weight of the sensor 10 helps to maintain the contact lens 40 in the orientation shown in FIGS. 9 and 10B.

The sensor 10 may be incorporated into the contact lens 40 at the inner surface 42 during the lens fabrication process. For example, if the contact lens 40 is made using a spin casting process, the lens solution is injected onto a spinning mold (not shown), with the spin rate and time being typically computer controlled. The sensor 10 may be placed in a pocket machined into the mold and held in place via vacuum. When the molding is complete, the vacuum is removed from the sensor 10, the contact lens 40 is removed from the mold and the contact lens with the sensor incorporated therein is handled using conventional procedures. Accordingly, the contact lens 40 including the sensor 10 may be a separate article of manufacture in accordance with one aspect of the present invention The apparatus 180 further comprises a hand-held eyepiece 182 with a relatively movable applanator 184 for manually applying force against the sensor 10 as described further below. The eyepiece 182 includes upper and lower arcuate ridges 184 and 186 for aligning the eyepiece in the patient's eye socket. The eyepiece 182 further includes an antenna 187 (shown schematically in FIG. 10A) for transmitting to and receiving electrical signals from the tank circuit on the sensor 10.

The applanator 184 resembles a plunger disposed in a cylinder and has a distal end 185. The distal end 185 is movable toward the eye 36 relative to the eyepiece 182 by pushing manually on a pushbutton mechanism 188. Internally, the motion of the applanator 184 may be opposed or biased by a spring (not shown) and/or a damper (not shown). Further, it is contemplated that movement of the pushbutton mechanism 188 may pressurize a balloon (not shown) inside the applanator 184 that causes the distal end 185 of the applanator to move toward the eye 36. Similarly, a bladder (not shown) of silicone gel could be compressed inside the applanator 184 by pressing the pushbutton mechanism 188 to cause the distal end 185 to move toward the eye. It is also contemplated that the applanator 184 could include a motorized and/or automated mechanism that is actuated by pressing the pushbutton mechanism 188 and which presses the distal end 185 against the eye 36.

As may be seen in FIG. 9, the applanator 184 projects outward at an angle from the eyepiece 182. The angle at which the applanator 184 projects is designed to place the distal end 185 perpendicular to the plane that the sensor 10 lies in when the contact lens 40 is positioned properly in the eye 36. As is discussed further below, the distal end 185 of the applanator 184 is used to press the contact surface 14 of the sensor 10 against the eye to obtain IOP measurements.

When the contact surface 14 of the sensor 10 is pressed against the surface portion 34 of the eye 36, the response of the sensor 10 over time is shown in the illustrations of FIGS. 11A1 through 11E2. Each of the FIGS. 11A through 11E provides an illustration of the position of the sensor 10 in relation to the eye 36 and a corresponding time graph of a pressure representative signal vs. time. The darkened region along each time graph is the time interval represented by the respective illustration. In FIG. 11A, advancing the sensor 10 toward the cornea 46 of the eye 36 causes the sensor to flex. In FIG. 11B, the compliant region 18 of the sensor 10 initially meets the surface portion 34 of the eye 36. The initial dip in pressure at point 60 from the base line pressure point 62 may be due to surface tension attracting the diaphragm 20 of the compliant region 18 just before actual contact with the surface portion 34 of the eye 36.

Accordingly, as the sensor 10 is pressed further against the surface portion 34 and the diaphragm 20 is depressed as shown in FIG. 11C, the pressure representative signal will continue to increase. As the flattening of the surface portion 34 increases, the sensed pressure peaks, as shown at point 64 in FIG. 11D, starts to decrease as a result of the bending forces of the cornea 46 being transferred from the compliant region 18 to across the non-compliant region 16 of the sensor 10. Point 64 represents the initial crest of the pressure representative signal. As the sensor 10 is pressed further against the surface portion 34 as shown in FIG. 11E, the pressure reaches a minimum at point 66 and this minimum represents the IOP of the eye 36. Thereafter, as the sensor 10 is moved farther toward and against the surface portion 34, the pressure increases beyond the IOP stage due primarily to an artificial elevation of IOP resulting from additional applanation and other forces in the eye 36, such as, surface tension from tearing shown at point 68, bending force shown at 70, and tissue tension shown at point 72, for example. After the IOP has been measured via the sensor 10, the sensor is returned back to its original starting position by the pushbutton mechanism 188, and the pressure reading is baselined at point 62. The sensor 10 is then ready to take another IOP measurement.

In order to take the IOP measurements from the sensor 10, a control unit 50 (FIGS. 10A and 12) is provided and is operatively coupled, in a manner not shown, to the antenna 187 in the eyepiece 182. The control unit 50 generates the activation signal for energizing the impedance element of the sensor 10 to measure a signal representative of the IOP. This activation signal is preferably an electromagnetic signal that varies over a predetermined radio frequency range say from one hundred to two hundred megahertz (100–200 MHz), for example, that energizes the tank circuit of the sensor 10 and causes it to resonate. The control unit 50 may also include a circuit to detect the resonant frequency of the sensor's tank circuit which is proportional to the IOP as shown by the graph of FIG. 5B, for example. This activation signal may be transmitted from the control unit 50 multiple times over a predetermined time interval during which the sensor 10 is in contact with the eye 36. Each electromagnetic activation signal is ramped from a starting frequency $f_1$ to an ending frequency $f_2$ in order for a resonant frequency to be determined which is representative of a pressure measurement sampling point during the application of the sensor 10 to the eye 36. The collection of this pressure measurement data (or sampling points) provides for a pressure vs. time graph, as exemplified by FIG. 11E, in order to determine the minimum or actual IOP.

Figure 12:
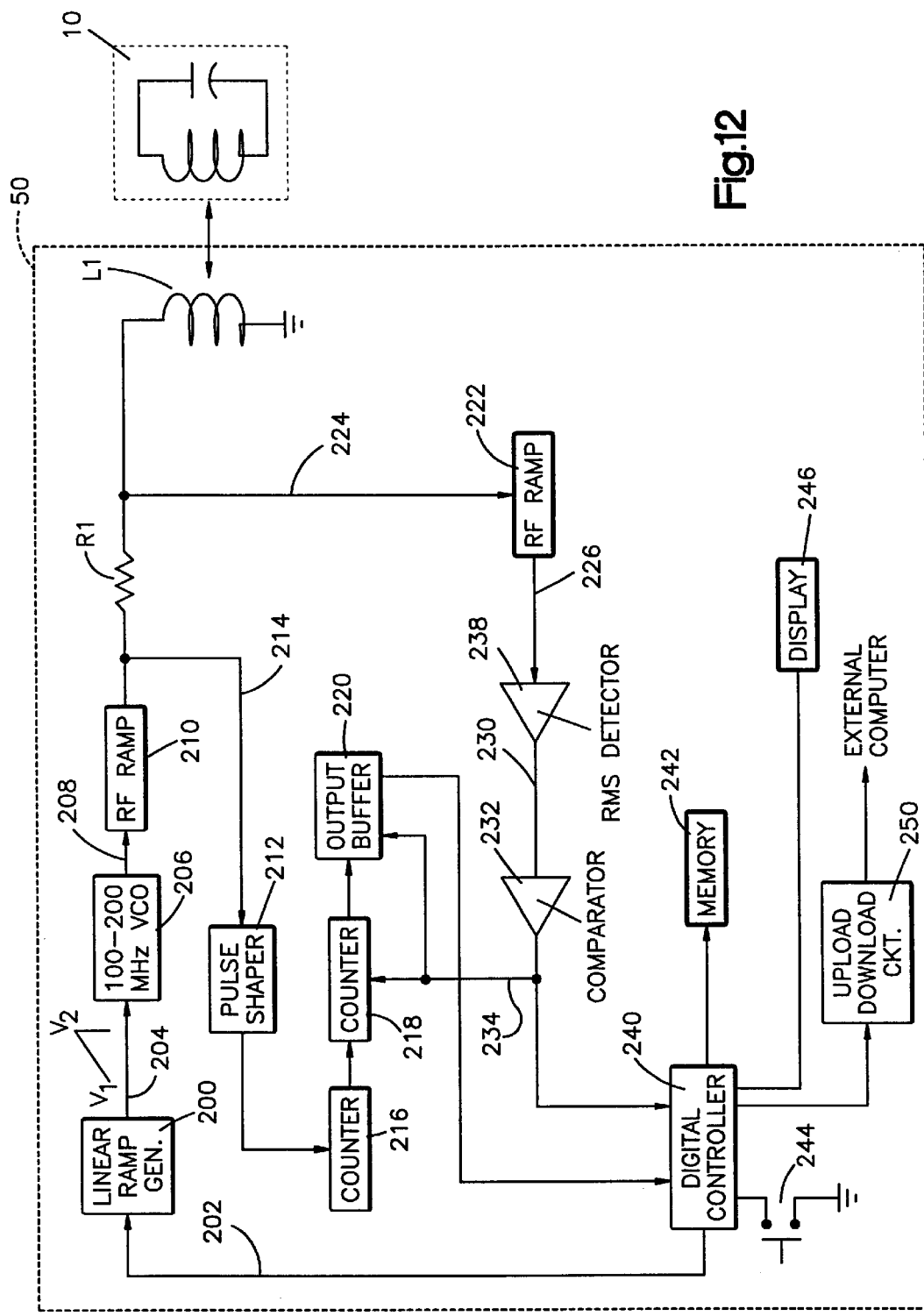
FIG. 12 is a functional block diagram schematic of a control unit for use with the apparatus of FIG. 9.

A schematic block diagram of the control unit 50 for use in of the present invention is shown in FIG. 12. Referring to FIG. 12, a circuit 200 may be triggered by a signal 202 to generate a linear ramping signal 204 which ranges from voltages V1 to V2 over a predetermined time interval Δt, on the order of 1 millisecond, for example. At the end of the time interval Δt, the voltage returns to a predetermined voltage setting to wait for the next trigger signal over line 202. The linear ramping signal 204 governs a voltage controlled oscillator (VCO) circuit 206 to generate a sinusoidal signal 208 which overlaps the frequency range of the sensor 10 as the signal 204 ramps from V1 to V2. The signal 208 may be amplified by a radio frequency (RF) amplifier circuit 210 which drives a resistor/inductor series combination, R1 and L1, respectively. The output of the RF amplifier 210 may be provided to a pulse shaper circuit 212 over signal line 214 which in turn is coupled to a cascaded pair of digital counters 216 and 218. The digital output of counter 218 is captured in an output buffer 220.

The voltage across the inductor L1 is input to another RF amplifier 222 via signal line 224. The output 226 of the RF amplifier 222 is provided to a root-mean-square (RMS) detector 228, the output 230 of which being coupled to a comparator circuit 232. In the present embodiment, the comparator circuit 232 functions as a signal peak or valley detector and generates a signal over line 234 when the signal peak or valley is detected. The signal line 234 is coupled to the counter 218 and output buffer 220 for operation thereof. The circuits of the control unit 50 may be centrally controlled in operation by a digital controller 240, which may be a programmed microprocessor, digital signal processor or a combination of hardwired digital logic circuits. A memory unit 242 is coupled to the digital controller 240 and may be comprised of a combination of static, dynamic and read-only memory units, for example, for the storage of data and program information. A switch 244 is coupled to the digital controller 240 through conventional input-output circuitry (not shown). The digital controller 240 may also be coupled to a conventional display unit 246 for displaying IOP readings. The control unit 50 may also include an upload/download circuit 250 for transmitting data between the digital controller 240 and an external computer, like a PC, for example, over a hardwired connection.

Taking an IOP reading using the sensor 10, including the apparatus 180 and the control unit 50, will now be described in connection with FIGS. 9, 10A, 10B, 11E, and 12. With the contact lens 40 positioned in the eye 36 as shown in FIG. 9, the eyepiece 182 is brought into engagement with the patient's eye socket. This provides a rough alignment of the distal end 185 of the applanator 184 with the sensor 10 in the contact lens 40. This alignment is important because only localized pressure on the contact lens 10 is desired, as pressure applied to the entire cornea 46 may result in artificially high IOP measurements.

With the patient's eyelids 190 closed, as may be seen in FIG. 9, the pushbutton mechanism 188 is manually pressed until the distal end 185 of the applanator 184 presses firmly against the eyelid which, in turn, causes the contact surface 14 of the sensor 10 to firmly engage the surface portion 34 of the eye 36.

As the applanator 184 is being moved toward the eye 36 as shown in FIG. 11A1, the switch 244 may be depressed for taking an IOP reading. In response to the depression of the switch 244, the digital controller 240 commences with a sequence of control operations to perform the IOP reading. Trigger signals are generated at predetermined times over signal line 202 to cause the linear ramp circuit 200 to generate the ramping signals which controls the VCO circuit 206 to drive the inductor L1 via RF amplifier circuit 210 and resistor R1. In turn, the inductor L1 is coupled magnetically to the inductor of the sensor 10 and electromagnetically activates and drives the tank circuit of the sensor. As has been described herein above, the capacitive element (compliant region 18) of the sensor 10 will change in impedance as it is forced against the surface portion 34 of the eye 36. This change in impedance will cause a change in circuit resonance. Sensor readings are thus taken at the points of resonance of the magnetically coupled circuits. More specifically, during the time interval of each frequency ramp, the RMS voltage across the inductor L1 is monitored by the circuits 222, 228, and 232 to establish the point in time of resonance. At resonance, a signal is generated by the comparator circuit 232 to the digital controller 240, the counter 218, and the output buffer 220. In response to this signal, the digital count of the counter 218 which is representative of the resonance frequency is captured in the output buffer 220 and subsequently, read by the controller 240 and stored in the memory 242. When the digital count has been read and stored, the control unit 50 may generate an audible signal indicating that a measurement has been taken, and the process may then be repeated. The stored digital counts of each of the frequency sweep time intervals represent sampled data points which together form the pressure profile of FIG. 11E. The digital controller 240 then processes these sampled data points to determine the current IOP reading, which may be day and time stamped and stored in the memory 242 and displayed in the digital display 246.

Figure 14:
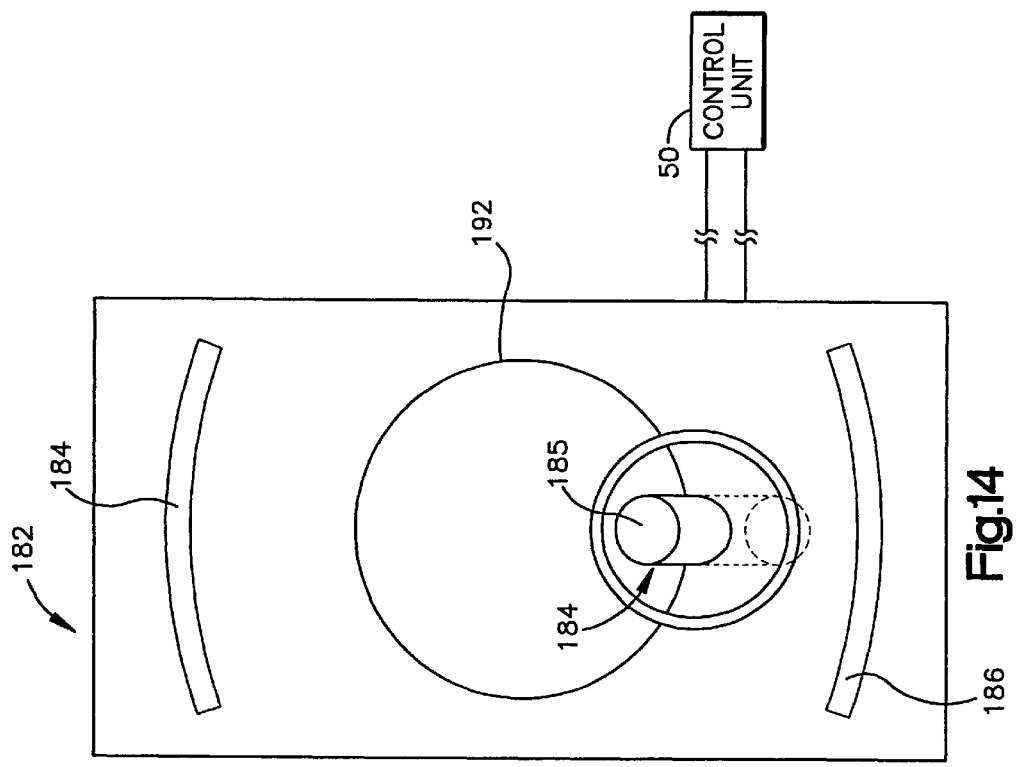
FIG. 14 is a sectional view taken along line 14—14 in FIG. 13.
Figure 13:
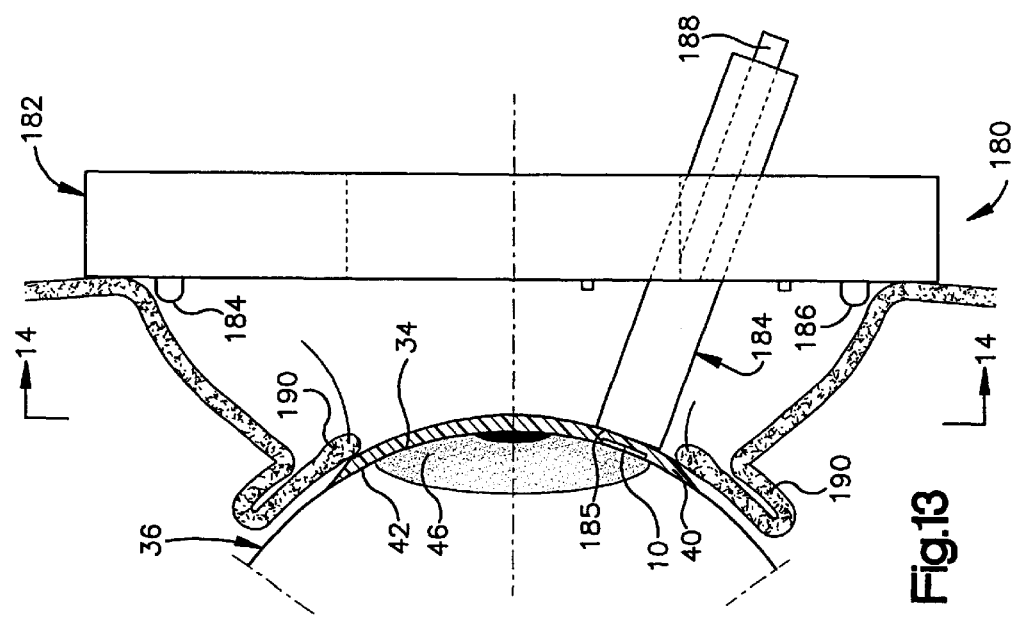
FIG. 13 is an illustration of an apparatus for measuring IOP in accordance with an alternate embodiment.

FIGS. 13 and 14 illustrate an alternate embodiment of the present invention in which the patient's eyelids 110 are open and the distal end 185 of the applanator 184 directly engages the contact lens 40 to apply pressure. In this embodiment, an aperture 192 is formed in the eyepiece 182 for the patient to look through.

From the above description of the invention, those skilled in the art will perceive improvements, changes and modifications. For example, it is contemplated that the applanator 184 could be disposed on the end of an instrument in a doctor's office, rather than a hand-held unit. It is further contemplated that other physical configurations of the applanator 184 could be used, such as a finger-mounted device which would, of course, include the antenna 190. Finally, it is conceivable that closed eyelids 190 may be able to supply sufficient pressure on their own to press the sensor 10 against the eye 36, in which case the eyepiece 182 would carry only the antenna 190 and not the applanator 184. Such improvements, changes and modifications within the skill of the art are intended to be covered by the appended claims.

Having described the invention, we claim:

1. An apparatus for measuring intraocular pressure of an eye, said apparatus comprising:
   a contact lens including an inner surface contoured to a surface portion of the eye for engaging the surface portion; and
   a sensor disposed in said inner surface of said contact lens, said sensor comprising:
      a contact surface for making contact with the surface portion of the eye, said contact surface including an outer non-compliant region and an inner compliant region fabricated as an impedance element that varies in impedance as said inner compliant region changes shape; and
      a region of conductive material electrically coupled to said impedance element of said compliant region and responsive to an external signal for energizing said impedance element so that the intraocular pressure may be determined.

2. The apparatus of claim 1 wherein said sensor is comprised of silicon material.

3. The apparatus of claim 1 wherein said sensor is comprised of a polymeric material.

4. The apparatus of claim 3 wherein said sensor comprises at least two layers of polymeric film bonded together.

5. The apparatus of claim 1 wherein said compliant region comprises a diaphragm that functions as one plate of a capacitive element, said diaphragm being separated by a dielectric region from another plate of said capacitive element, said diaphragm flexing closer to said other plate as said contact surface is pressed against the surface portion of the eye to change the capacitance of said capacitive element in proportion to the intraocular pressure of the eye.

6. The apparatus of claim 5 wherein said dielectric region comprises air.

7. The apparatus of claim 5 wherein said dielectric region comprises hydrogel.

8. The apparatus of claim 5 wherein said dielectric region comprises silicone.

9. The apparatus of claim 5 wherein said region of conductive material comprises an inductor coil that is electrically coupled to said capacitive element to form a resonant circuit, the external signal comprising an electromagnetic signal that varies in frequency to cause said resonant circuit to be energized and resonant at a frequency in proportion to the capacitance of said capacitive element so that the intraocular pressure may be determined.

10. The apparatus of claim 9 wherein said inductor coil is fabricated in said non-compliant region.

11. The apparatus of claim 9 wherein said inductor coil is fabricated on said inner compliant region.

12. The apparatus of claim 11 further comprising a second inductor coil formed underneath said diaphragm.

13. The apparatus of claim 9 wherein said inductor coil is formed by disposing conductive material in a predetermined pattern in a surface of said non-compliant region about said compliant region of said contact surface.

14. The apparatus of claim 9 further comprising an applanator for applying pressure against said contact lens to cause said contact surface of said sensor to firmly engage the surface portion of the eye.

15. The apparatus of claim 14 further comprising an eyepiece for covering over the eye, said applanator being mounted in and movable relative to said eyepiece.

16. The apparatus of claim 15 further comprising an antenna disposed on said eyepiece, said antenna for transmitting the external signal for energizing said impedance element.

17. The apparatus of claim 16 further comprising a control unit for generating the external signal to measure a signal representative of intraocular pressure, said control unit being operatively coupled with said antenna.

18. The apparatus of claim 17 wherein said compliant region comprises a capacitive element that changes capacitance in proportion to a change in shape, said region of conductive material comprising an inductive coil electrically coupled to said capacitive element to form a resonant circuit.

19. The apparatus of claim 18 wherein said control unit generates an electromagnetic signal that varies over a predetermined frequency range to cause said resonant circuit to resonate, said control unit including means for measuring the resonant frequency of said resonant circuit which is representative of the intraocular pressure of the eye.

20. The apparatus of claim 17 wherein said control unit includes processing means for measuring signals representative of intraocular pressure at different times during a predetermined time interval, and a memory for storing the measured signals representative of the intraocular pressure measured at said different times.

21. The apparatus of claim 20 wherein said control unit includes means for processing the stored measured signals representative of intraocular pressure to determine a resultant intraocular pressure (IOP) measurement.

22. The apparatus of claim 21 wherein said control unit includes means for time marking each resultant IOP measurement with a measurement time and for storing said resultant IOP measurements with their corresponding measurement times in the memory.

23. The apparatus of claim 22 wherein said control unit includes means for transferring the stored resultant IOP measurements and their corresponding measurement times to another system.

24. The apparatus of claim 17 wherein said control unit includes a display for displaying the intraocular pressure measurements.

25. A method for measuring intraocular pressure (IOP) of an eye, said method comprising the steps of:
   providing a contact lens having an inner surface contoured to a surface portion of the eye, the contact lens including a sensor disposed in the inner surface of the contact lens, the sensor having a compliant region that functions as an impedance element;
   positioning the contact lens on the surface portion of the eye;
   providing an applanator for applying pressure against the contact lens;
   moving the applanator toward the eye until the sensor forcefully engages the surface portion of the eye which causes the compliant region to change shape and vary in impedance;
   energizing the impedance element;
   determining a representative pressure measurement each time the impedance element is energized; and
   processing the representative pressure measurements to render a resultant IOP measurement.

26. The method of claim 25 wherein said step of energizing the impedance element includes the step of:

energizing an inductive region of the sensor that is connected to the impedance element which is a capacitive region to cause a circuit formed by the regions to resonate.

27. The method of claim 26 wherein said step of energizing an inductive region of the sensor includes transmitting an activation signal over an antenna.

28. The method of claim 26 wherein said step of energizing the impedance element includes generating an electromagnetic signal with a frequency that is swept through a frequency range over a predetermined time interval, the resonant frequency of the circuit falling within said frequency range.

29. The method of claim 28 wherein said step of determining includes the steps of determining the resonant frequency of the circuit each time the circuit is energized, the resonant frequencies sampled being representative of the IOP of the eye at different times.

30. The method of claim 29 wherein said step of processing includes processing the sampled resonant frequencies to render a resultant IOP measurement.

31. The method of claim 30 further comprising the steps of:
  time marking each resultant IOP measurement; and
  storing each IOP measurement along with its corresponding measurement time.

32. The method of claim 31 further comprising the step of transmitting the stored IOP measurements and their corresponding measurement times to an external site.

33. The method of claim 32 wherein said steps of energizing, determining and processing are performed autonomously by a control unit.

34. The method of claim 33 further comprising the step of displaying the resultant IOP measurement on the control unit.

* * * * *